United States Patent [19]

Dines et al.

[11] Patent Number: 4,520,133
[45] Date of Patent: May 28, 1985

[54] MONOHYDROXY-BENZOYL PEROXIDE AND COMPOSITIONS FOR TREATING ACNE

[75] Inventors: Allen I. Dines, Danbury; David Yeung, Stamford; Sergio Nacht, Weston, all of Conn.

[73] Assignee: Richardson-Vicks Inc., Wilton, Conn.

[21] Appl. No.: 522,207

[22] Filed: Aug. 11, 1983

[51] Int. Cl.³ .................. A61K 31/075; C07C 179/15
[52] U.S. Cl. .............................. 514/568; 260/453 RZ
[58] Field of Search ................ 260/453 RZ; 424/338; 514/568

[56] References Cited

U.S. PATENT DOCUMENTS 4,279,831 7/1981 Halle et al. ................... 260/453 RZ
4,318,907 3/1982 Kligman et al. .................... 424/230
4,355,028 10/1982 Kligman et al. .................... 424/230

Primary Examiner—Henry R. Jiles
Assistant Examiner—Robert C. Whittenbaugh
Attorney, Agent, or Firm—George W. Rauchfuss, Jr.; Salvatore R. Conte

[57] ABSTRACT

Monohydroxy-benzoyl peroxide of the formula

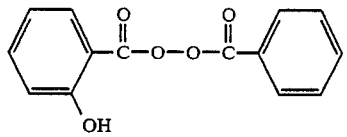

possesses both antibacterial and comedolytic activity and is useful in compositions for the treatment of acne.

5 Claims, No Drawings

MONOHYDROXY-BENZOYL PEROXIDE AND COMPOSITIONS FOR TREATING ACNE

FIELD OF THE INVENTION

The present invention relates to a novel compound possessing both antibacterial and comedolytic activity and to compositions thereof for the treatment of acne.

BACKGROUND OF THE INVENTION

Acne is a disease of the pilosebaceous units of the skin and is characterized by the formation of comedones (whiteheads and blackheads); inflamatory papules; pustules and in more severe cases, inflammatory granulomas (cysts) and hypertrophic scars. Topical treatments for acne are mainly aimed at reducing the number of comedones and the intensity of inflammation. There are three known factors which are important in the pathogenesis of acne: (1) hyperactive sebaceous gland, (2) obstruction to the pilosebaceous apparatus by excessive keratinization of the follicula epithelial, and (3) initiation of the inflammatory process by a skin bacteria: *Propionibacterium acnes*.

Various treatments of acne are primarily focused on the three aforementioned factors. The suppression of sebaceous gland activity or sebum excretion rate can now be accomplished by the oral 13-cis retinoic acid therapy. The correction of the abnormal or excessive keratinization is accomplished by topical treatment with comedolytic agents such as transretinoic acid and salicylic acid which are effective in reducing the number of comedones. Reduction of the inflammation process can be achieved by the topical application of potent antimicrobial agent such as benzoyl peroxide which is extremely effective in reducing the number of the acne bacillus, *Propionibacterium acnes*.

However, the comedolytic agent salicylic acid does not possess any antibacterial activity against *P. acnes* nor does benzoyl peroxide possess any significant comedolytic activity. Recently, in U.S. Pat. No. 4,355,028, issued Oct. 19, 1982 to A. Kligman et al. it has been proposed to treat acne vulgaris with both salicylic acid and benzoyl peroxide at certain specified levels simultaneously or sequentially.

It is therefore highly desirable that a compound possessing both comedolytic and antibacterial activity against *P. acnes* be found to provide for a simplified yet improved treatment of acne and particularly acne vulgaris.

SUMMARY OF THE INVENTION

It has now been found that monohydroxy benzoyl peroxide of the formula

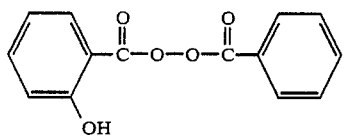

possesses both antibacterial activity against *P. acnes* and comedolytic activity and is useful in the treatment of acne by topical application of compositions thereof in the form of creams, lotions, gels or solutions containing said compound in an amount of from about 1% to about 20%, preferably from about 2.5% to 10% by weight. The novel compound of the invention has been found to be even more active against acne than benzoyl peroxide. The compositions are applied to the acne affected area of skin in an anti-acne effective amount.

DETAILS OF THE INVENTION

The novel monohydroxy-benzoyl peroxide of this invention is prepared by reacting salicyloyl chloride with perbenzoic acid. Preparation of the monohydroxybenzoyl peroxide of this invention is illustrated in the following Example.

EXAMPLE

To one mole (138 gm) of salicylic acid in 250 ml of benzene, 0.5 ml of pyridine and 130 gm of thionyl chloride (1.1 mole) were added. The mixture was stirred at room temperature for about two hours, followed by warming at 50° C. until the mixture was homogeneous and the evolution of HCl has ceased. The benzene and excess thionyl chloride were removed in vacuo on a rotary evaporator. The resulting faintly yellow oil was crystallized in the freezer upon storage.

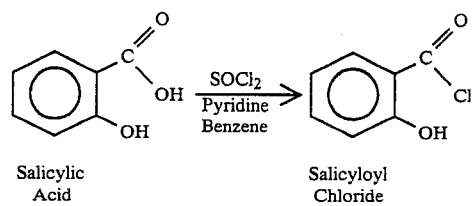

Salicylic Acid → Salicyloyl Chloride

One mole of benzoyl peroxide (250 g) was dissolved in 1000 ml of chloroform and cooled to 0° C. in an ice bath. The solution was then added portionwise with stirring to a solution of sodium methoxide (26 gm sodium metal in 500 ml methanol) in an ice-salt bath. The resulting perbenzoic acid salt was extracted twice with cold chloroform to remove impurities. The salt was then converted to acid and back extracted into chloroform. The amount of perbenzoic acid was determined by titrating the mixture with sodium thiosulfate solution. An equal molar (0.45 mole) of salicyloyl chloride was then added to the perbenzoic acid mixture. The solution was cooled to 0° C. and then 0.64 mole of pyridine in 100 ml dichloromethane was added dropwise over a period of 25 minutes. The reaction was continued for 20 minutes after the addition. The reaction mixture was extracted with methylene chloride and the organic layer was washed with dilute HCl solution, water and then sodium carbonate. The organic layer was then dried over anhydrous $Na_2SO_4$. The solvent was then removed in vacuum and a red-oil was obtained.

This red-oil like material was dissolved in benzene and passed through a column packed with silica gel; the mobile phase was benzene. Fractions of the element were collected and monitored by thin layer chromatography. The fraction which gave a reaction (red spot) with $Fe(NH_4)SO_4$ solution was collected and the solvent in this fraction was evaporated under vacuum. This resulted in an oil which crystallized upon shaking with cold hexane-ether (9:1) and cooling. The crystals were filtered and subjected to various analytical characterization.

The monohydroxy-benzoyl peroxide is a white crystalline material with a melting point of 102°–103° C. Ultra-violet spectroscopic analysis gave characteristic absorption peaks at 277, 282, and 310 nanometers, with extinction coefficients of 2260, 2285, and 2950 respectively. It appears to be stable at room temperature without any sign of physical degradation.

The active ingredient can be incorporated in a variety of vehicles for topical application to the skin for treatment of acne. Such vehicles, in the form of creams, gels, lotions and solutions are known in the art and from about 1% to 20%, preferably about 2.5% to 10% by weight of said active ingredient can be incorporated in any such vehicles to provide anti-acne compositions of this invention. Illustration of one such composition is the following lotion vehicle:

| Ingredients | % w/w |
| --- | --- |
| Polyethylene Glycol-100 Stearate | 2.65 |
| Glyceryl Stearate | 2.50 |
| Cetyl Alcohol | 2.10 |
| Glycereth-26 | 2.00 |
| Isocetyl Stearate | 1.28 |
| Glycerin | 1.00 |
| Dimethicone Copolyol | 1.00 |
| Sodium Citrate | 0.50 |
| Citric Acid | 0.35 |
| Isopropyl Stearate | 3.00 |
| Methylparaben | 0.18 |
| Propylparaben | 0.02 |
| Camphor | 0.05 |
| Menthol | 0.20 |
| Aluminum Hydroxide | 0.05 |
| Purified Water | 78.17 |

The above described lotion vehicle was used in the following efficacy studies of the monohydroxy-benzoyl peroxide.

Minimum Inhibition Concentration (MIC) Study

This study was conducted to determine the minimum bactericidal concentration of various actives required to inhibit the growth of the *P. acnes*. The procedure of the study was as follows:

The testing procedure is an Agar Dilution Test designed for products which are insoluble and/or precipitate rendering culture media cloudy and making turbidimetric measurement of microbial growth difficult.

Twenty-four hours broth cultures of *P. acnes* ATTC# 11828 is prepared by adding a loopful (3 mm diameter loop) of the stock cultures to tubes containing nutrient broth. Trypticase Soy Agar is then melted and cooled to 45° C. in a water bath. 5 ml of agar are then transferred into each of the 10 labeled test tubes. Five ml of test sample is then put into tube #1 and the mixture is vortexed, this is a 1:2 dilution, then 5 ml of the tube #1 mixture is removed and placed in tube #2 containing 5 ml of agar, this is a 1:4 dilution. This procedure is continued to obtain a serial dilutions of the tested product. Five ml of the mixture from the last tube in the dilution series is discarded and contents of each tube (5 ml) are poured into a 30×10 petri dish after all serial dilutions have been made. Agar is allowed to solidify. In addition, control agar plates without the material under test are included to demonstrate the absence of activity of the agar medium. With a sterile pasteur pipette, one drop of the diluted *P. acnes* is placed on each agar plate and the plates are incubated at 35° C. in oxygen free environment for 3 to 4 days. The plates are then assessed for the presence or absence of growth of the *P. acnes*.

The endpoint of bacteriostatic activity is between the last plate with no growth and the first plate with growth.

The following compounds were tested:
(a) Benzoyl peroxide
(b) Monohydroxy-benzoyl peroxide
(c) Salicylic acid
(d) Benzoic acid The results of the MIC testings were as follows:

| Test Compound | Minimum Inhibition Concentration Against P. acnes ($\mu$g/ml) |
| --- | --- |
| Monohydroxy-benzoyl peroxide | 125 |
| Benzoyl peroxide | 125 |
| Benzoic acid | 2,000 |
| Salicylic acid | no activity |

As the results summarized in the above table indicate, the monohydroxy-benzoyl peroxide is active against the anaerobic bacteria *P. acnes* with a minimum inhibition concentration of 125 ug/ml. Benzoyl peroxide also exhibits a MIC of 125 ug/ml.

In-Vivo Antimicrobial Efficacy Testing

The study was designed to assess the in-vivo antimicrobial efficacy of the formulation containing the tested compound against anaerobic microflora *P. acnes*. The design and procedure of the study are as follows:

Format of the Study: Half face, with b.i.d. application to the cheek of each subject.

Subjects: Three males of 25–45 years of age with adequate number of *P. acnes* on their facial skin and of free fatty acid concentration on their skin surface lipids; as documented by the history of the microflora of each subject's facial skin from previous studies.

Duration of the Study: Fifteen days of test agent usage.

Usage regimen: Product application was for 11 consecutive days to the right or left cheek of each subject. The other cheek serves as the untreated control. The sampling was done 12–16 hours after product application. A non-active Lowila soap was used by all the subjects during this study.

Determination of Antibacterial Effects

The following parameters were measured:
(a) Skin flora *P. acnes* samples are obtained and quantified by the technique described by Williamson and Kligman (1).
(b) Free fatty acid concentration in skin surface lipids is determined by the method of Downing (2).

(1) Williamson, P. Kligman, A. M.: J. Invest. Dermatology 45:498–503, 1965.
(2) Downing, D. J.: Chromotography, 38:91–99, 1968.

Evaluation: Three to four days prior to the first product application, samples of the skin flora and of skin surface lipids were obtained from the cheeks of each subject as baseline measurements. Thereafter, samples were obtained on Day 1, 4, 8 and 15, with sampling done 16 hours after the last product application. Treatment stops on Day 15 as the last sampling is done on day 15 (16 hours after the last application).

Results: The results are expressed as the percent and log reductions in bacteria and as % free fatty acid reduction of the skin surface lipids over baseline or control values.

The product tested is a 5% monohydroxy-benzoyl peroxide in the aforementioned lotion vehicle.

In Vivo Antibacterial Efficacy

The following table summarizes the % or log reduction of the anaerobic skin flora *P. acnes* at different days after initiation of treatment.

| | Days of Treatment | | | | | | | |
|---|---|---|---|---|---|---|---|---|
| | 1 | | 4 | | 8 | | 15 | |
| Subject | % Reduction | Log Reduction | % Reduction | Log Reduction | % Reduction | Log Reduction | % Reduction | Log Reduction |
| A | >99 | 3.63 | >99 | 4.79 | >99 | 1.82 | 96 | 1.40 |
| B | >99 | 4.69 | 95 | 1.34 | 99 | 1.92 | — | — |
| C | 97 | 1.55 | 85 | 0.82 | 99 | 2.61 | >99 | 2.60 |
| Average | | 3.29 | | 2.32 | | 2.12 | | 2.00 |

Significant average reduction (>99%) in the anaerobic skin flora was observed in all three subjects as early as one day after initiation of product treatment. Thereafter, all subjects displayed significant reductions of the *P. acnes* during the course of the study.

We claim:
1. 2-Hydroxy benzoyl peroxide of the formula

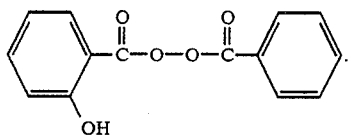

2. A composition for the topical treatment of acne in the form of a lotion, cream, gel or solution containing from about 1 to about 20% by weight of 2-hydroxy benzoyl peroxide of the formula

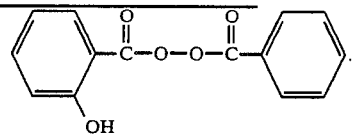

3. A composition of claim 2 wherein 2-hydroxy benzoyl peroxide is present in an amount of from about 2.5 to 10% by weight.

4. A process for treating acne comprising applying to the acne-affected area of the skin an anti-acne effective amount of a composition of claim 2.

5. A process for treating acne comprising applying to the acne-affected area of the skin an anti-acne effective amount of a composition of claim 3.

* * * * *